United States Patent [19]

Brinckmann et al.

[11] 4,008,720

[45] Feb. 22, 1977

[54] BLADE WITH IRRIGATION TUBES

[76] Inventors: Paul Brinckmann, Rinscheweg 11, 44 Munster; Joachim-Ulrich Krenz, Lindenstr 24, 4401 Roxel; Werner Ruck, Am Edelkamp 15, 4401 Holenholte, all of Germany

[22] Filed: June 2, 1975

[21] Appl. No.: 582,633

[30] Foreign Application Priority Data

June 8, 1974 Germany ............................ 2427716

[52] U.S. Cl. ............................... 128/317; 30/123.3; 83/169; 83/171

[51] Int. Cl.² ........................ A61B 17/14; B26D 7/08

[58] Field of Search ............ 30/123.3; 83/169, 171; 128/317

[56] References Cited

UNITED STATES PATENTS

| 197,650 | 11/1877 | Milligan | 83/171 |
| 1,628,315 | 5/1929 | Hamilton | 30/123.3 |
| 2,557,364 | 6/1951 | Treace | 128/317 |
| 2,854,981 | 10/1958 | Morrison | 128/317 |
| 3,554,197 | 1/1971 | Dobbie | 128/317 |

FOREIGN PATENTS OR APPLICATIONS

| 162,803 | 4/1958 | Sweden | 30/123.3 |
| 768,337 | 2/1957 | United Kingdom | 83/171 |

*Primary Examiner* — Channing L. Pace
*Attorney, Agent, or Firm* — Woodhams, Blanchard and Flynn

[57] ABSTRACT

A bone saw for medical purposes having a saw blade carrying out a back and forth movement. Channels for guiding a cooling medium are formed in the saw blade, which channels are connected to a cooling medium source.

7 Claims, 3 Drawing Figures

4,008,720

BLADE WITH IRRIGATION TUBES

FIELD OF THE INVENTION

The invention relates to a bone saw for medical purposes having a saw blade which carries out a back and forth movement and which is exposed to a cooling medium supply.

BACKGROUND OF THE INVENTION

A bone saw for medical purposes is already known which uses a back and forth moving saw blade. There is also known a bone saw for medical purposes which consists of two oppositely rotating spaced apart saw blades, whereby between the saw blades a cooling liquid is supplied and thus exits in the direct work range of the saw blades. Such an arrangement is structurally expensive and furthermore has the disadvantage that a plugging up of the space between the two saw blades can occur, which can jeopardize the effective supply of the cooling liquid.

There is also known a cooling device for a rotatable circular saw which is used for treating of wood, stone and metal. In this known device, cooling medium channels are installed in the circular saw blade, which channels open out at the periphery of the saw blade. The cooling medium is supplied centrally through the drive shaft of the saw blade. However, this construction causes a weakening of the actual cutting surface of the saw blade. Furthermore, this known device has the disadvantage that a sufficient cooling effect is not achieved because the actual saw blade is being cooled only in the area of the channels, so that an effective discharge of the heat in the cutting area of the saw blade is not achieved. Also in this known device, a plugging up of the channel ports must be feared. To avoid this danger, the cooling medium pressure is increased, whereupon a washing off of the cooling liquid in the saw cut occurs. If such a construction were to be used for medical purposes, there exists the danger that through the rebound of fine spray, the open wound cannot be kept free from contamination.

The basic purpose of the invention is to produce a saw blade for medical purposes which has a cooling medium infeed, in which the cooling medium outlet is arranged in such a manner that an effective cooling of the entire blade area including the adjoining walls of the bone to be treated takes place.

The basic purpose of the invention is attained by forming channels for conducting the cooling medium in the saw blade, which channels open out in the front area of the saw blade to the two outer sides of the saw blade. Through this arrangement a plurality of advantages compared with the presently known constructions is achieved. Thus it is assured that plugging of the channel ports through bone splinters and soft particles is not possible. The pressure for suplying the cooling medium can be kept low, so that the exiting cooling fluid does not interfere in the operation area. The saw blade has, in spite of the cooling medium channels which are worked into same, in particular in its substantially stressed area, namely on the periphery, a sufficient stability and the saw blade operates in a cooling medium layer, which is provided on both sides of the blade area and of the adjoining bone walls, through which especially the most important area of the bone is cooled. The bone particles are transported away through the liquid polster on both sides of the teeth of the saw in a particularly advantageous manner.

A practical construction of the inventive suggestion can best be realized by the channels being formed by slots which are open toward both saw blade surfaces, into which slots small tubes or the like are inserted stationarily, whereby the outer surface is again worked completely smoothly. Such a construction appears to be technically simpler and less complicated in manufacture than drilling into the relatively thin saw blade.

To achieve a problemless exit of the cooling medium, it is furthermore suggested that guide devices are arranged at the outlet end of the channels, which guide the cooling fluid on both sides of the saw blade.

The inventive saw blade offers moreover the advantage, that during the sawing operation of the created wound additional materials can be supplied, as for example antibiotic means or the like, so that aside from the actual cooling operation an additional medical effect can be achieved.

BRIEF DESCRIPTION OF THE DRAWINGS

One exemplary embodiment of the invention will be discussed hereinafter in connection with the drawing, in which.

DETAILED DESCRIPTION

Figure 1:
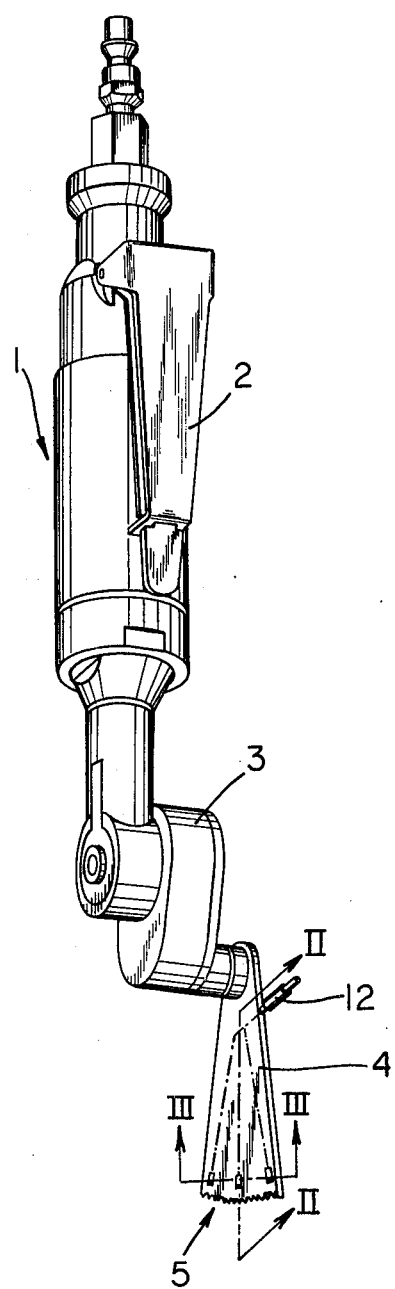
FIG. 1 illustrates a bone saw equipped with the inventive saw blade.

FIG. 1 illustrates a conventional bone saw generally designated with reference numeral 1, which can be driven by pressurized air, whereby reference numeral 2 identifies the handle which is used to operate the device. A transmission gear 3 can take care of desired changes of the number of oscillations of the actual saw blade 4.

The saw blade 4 is constructed substantially triangularly in a conventional manner, whereby the apex of the triangle is drivingly connected to the gear device 3, while on the opposite side of the front area of the saw blade exists, which is identified by reference numeral 5 and which has correspondingly set saw teeth.

Figure 2:
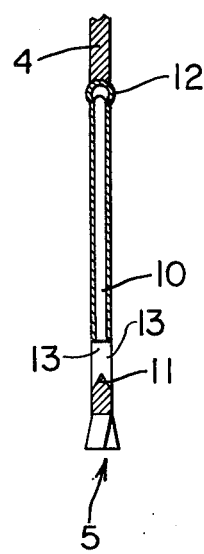
FIG. 2 illustrates on an enlarged scale a cross-sectional view along the line 2—2 of FIG. 1.
Figure 3:
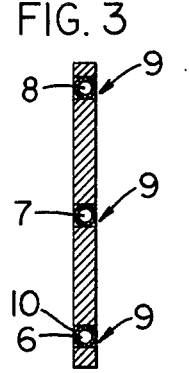
FIG. 3 illustrates also in an enlarged scale a cross-sectional view along the line 3—3 of FIG. 1.

Radially extending channels 6, 7 and 8 are worked into this saw blade, as this is clearly shown in FIGS. 2 and 3, namely in the illustrated exemplary embodiment in such a manner that slots 9 are provided in the saw blade, into which small tubes 10 are embedded. The free spaces are again filled in with a corresponding soldering means or the like, so that after insertion of the small tube 10 a smooth saw blade surface is obtained. The individual channels 6 to 8 end spaced from the front area of the saw blade, which is particularly clearly shown in FIG. 2, and guide devices are provided in this front area within the saw blade, of which guide devices the guide device 11 can be recognized in FIG. 2. This guide device 11 is shaped as a tapered member having the apex thereof directed toward the discharge end of the tube 10 so as to cause the cooling medium stream exiting from the small tube 10 is to be deflected sidewardly in opposite directions for discharge through the openings 13 so that the cooling medium is directed evenly on both surfaces of the saw blade.

On the inner end, the small tubes 10 are connected to a supply line 12 which has a connection device for a flexible connecting means, for example a plastic hose or the like, which serves to supply the cooling medium.

Distilled water or a special liquid can usually be used as the cooling medium, which also effects suitable medical effects.

Due to the fact that the small tubes 10 end spaced from the front area (that is, the teeth) of the saw blade 5, the necessary stability of the saw blade is assured in this area which is most highly stressed.

Even though this is not illustrated in the drawing, and the illustrated embodiment is considered the technically simple one, it is of course possible to obtain the channels which serve to guide the cooling medium within the saw blade by drilling the saw blade.

Although a particular preferred embodiment of the invention has been disclosed in detail for illustrative purposes, it will be recognized that variations or modifications of parts, lie within the scope of the present invention.

The embodiments of the invention in which an exclusive property or privilege is claimed are defined as follows:

1. In a bone saw having a housing, a saw blade movably supported on said housing for oscillating movement, the blade being of a thin and substantially planar sheetlike material having opposed substantially flat side surfaces, the blade having thereon, outer arcuate peripheral edge portion having saw teeth formed thereofn, and drive means connected to said blade at a location spaced radially inwardly a substantial distance from said teeth for causing oscillatory movement of said blade about a pivot axis, comprising the improvement wherein said blade has a plurality of elongated distributing channels formed therein for guiding a fluid cooling medium therethrough, said channels extending inwardly of said blade from said saw teeth toward said pivot axis, said distributing channels each having an inner end thereof disposed more closely adjacent said pivot axis and an outer end thereof disposed more closely adjacent said teeth, a supply channel formed in said blade and communicating with said one end of each of said distributing channels, said supply channel being adapted for connection to a source of said cooling medium, said blade having a plurality of openings extending axially therethrough from one side surface of said blade to the other side surface thereof, said openings being disposed closely adjacent but spaced radially inwardly a small distance from said saw teeth, each said distributing channel having said other end thereof in open communication with one of said openings, diverter means fixedly associated with said blade and disposed adjacent the radially outer edge of each said opening for deflecting the cooling medium discharged from said other end of said distributing channels sidewardly in opposite directions so that said cooling medium flows outwardly through opposite ends of each said opening and then flows along the opposite side surfaces of said blade and along the opposite sides of said saw teeth.

2. In a bone saw according to claim 1, wherein said diverter means comprises a tapered portion which defines the radially outer edge of said opening and which projects toward said other end of the respective distributing channel so that said tapered portion has the apex thereof disposed opposite but spaced from said other end of said distributing channel to thereby deflect the flowing stream of cooling medium into substantially equal parts which flow outwardly through opposite ends of said opening.

3. In a bone saw according to claim 1, wherein said distributing channels are totally closed except for openings defined at the opposite ends thereof, said distributing channels being defined solely between the opposite side surfaces of said blade so that said side surfaces are substantially planar and are substantially parallel to one another.

4. In a bone saw according to claim 1, wherein said blade has a plurality of elongated slots formed therein, each of said slots extending from said supply conduit to a respective one of said openings, said slots extending completely through the width of said blade from one side surface thereof to the other side surface thereof, and each said distributing channel comprising an elongated tubular element positioned within and extending longitudinally throughout the length of said slot, said tubular element being fixed to said blade and confined totally within said blade so that the side surfaces of said blade are substantially flat.

5. A bone saw for medical purposes having a saw blade for carrying out a back-and-forth movement, the saw blade being of a thin, flat, platelike structure which includes opposed and substantially parallel flat side surfaces, said blade having a peripheral edge with saw teeth formed therealong, the improvement wherein the blade is provided with internal means for supplying a flowable fluid cooling medium to the peripheral edge having the saw teeth formed thereon, said internal means including a plurality of elongated distributing passages formed internally of said blade, each of said distributing passages being closed except for openings provided at the opposite ends thereof, the opening at one end of each said distributing passage being disposed at a first location which is spaced a substantial distance from the peripheral edge of said blade, and the opening at the other end of each said distributing passage being disposed closely adjacent said peripheral edge but spaced slightly inwardly therefrom, supply passage means associated with the openings formed in said one ends of said distributing passages for supplying said cooling medium thereto, and diverter means fixedly associated with said blade and disposed adjacent the openings formed at the other ends of said distributing passages for causing the stream of cooling medium which is discharged from each said distributing passage to be divided into two sub-streams which are deflected sidewardly in opposite directions so as to flow along the opposite side surfaces of said blade and along the opposite sides of the saw teeth.

6. A bone saw according to claim 5, wherein said saw blade has a plurality of transverse openings formed therein and extending transversely therethrough from one side surface to the other side surface thereof, said transverse openings being disposed closely adjacent but spaced inwardly from said peripheral edge so that one of said transverse openings is disposed adjacent said other end of each said distributing passage, whereby each of said distributing passages discharges a stream of cooling medium into one of said transverse openings, and said diverter means being positioned along an edge of each said transverse opening which is disposed opposite from the discharge end of the respective distributing passage for dividing the discharged stream of cooling medium into said two sub-streams which are deflected sidewardly in opposite directions so as to flow outwardly through the opposite ends of said transverse opening.

7. A bone saw according to claim 6, wherein said blade has a plurality of elongated slots formed therein, each of said slots being associated with one of said distributing passages and extending from said first location to one of said transverse openings, and said distributing passage being defined by an elongated tubular member which is separate from said blade member but is disposed within said slot and is fixedly secured to said blade member, and said tubular member being confined totally between the side surfaces of the blade so that said side surfaces are substantially flat.

* * * * *